United States Patent [19]

Hesse

[11] Patent Number: Plant 6,223

[45] Date of Patent: Jul. 12, 1988

[54] CHRYSANTHEMUM PLANT NAMED YELLOW DYNAMO

[75] Inventor: Peter S. Hesse, Bradenton, Fla.

[73] Assignee: Ball PanAm Plant Company, Parrish, Fla.

[21] Appl. No.: 892,089

[22] Filed: Aug. 1, 1986

[51] Int. Cl.[4] ..... A01H 5/00

[52] U.S. Cl. ..... Plt./78

[58] Field of Search ..... Plt./78

*Primary Examiner*—James R. Feyrer

*Attorney, Agent, or Firm*—Schwartz, Jeffery, Schwaab, Mack, Blumenthal & Evans

[57] ABSTRACT

A Chrysanthemum plant named Yellow Dynamo having strong stems with long peduncles that carry bright, deep yellow flowers; nine week response; excellent production per stem; good shipping and keeping qualities, and adaptability to year around programs.

1 Drawing Sheet

The present invention comprises a new and distinct cultivar of *Chrysanthemum morifolium*, Ramat., hereinafter referred to by the cultivar name Yellow Dynamo.

Yellow Dynamo is a mutation from Dynamo, disclosed in a pending application of Leonard H. Shoesmith. Yellow Dynamo was originated in a mutation breeding program, the primary purpose of which was to expand the color (white) of Dynamo. The program was conducted by or under the supervision of applicant in 1981 in Parrish, Fla. Tissue cultured plants of the parent cultivar Dynamo were exposed to 2,000 rads of X-ray energy. Yellow Dynamo was discovered and selected from a bed of irradiated parent plants on June 4, 1981 by applicant in a controlled environment in Parrish, Fla.

The first act of asexual reproduction of Yellow Dynamo was accomplished when vegetative cuttings were taken from the initial selection in August of 1981 in a controlled environment in Parrish, Fla. by a technician working under formulations established and supervised by applicant. Horticultural examination of selected units initiated in November of 1981 has demonstrated that the combination of characteristics as herein disclosed for Yellow Dynamo are firmly fixed and are retained through successive generations of asexual reproduction.

Yellow Dynamo has not been observed under all possible environmental conditions. The phenotype may vary significantly with variations in environment such as temperature, light intensity, and day length. The following observations, measurements and comparisons describe plants grown in Parrish, Fla. under greenhouse conditions which approximate those generally used in commercial practice.

The following traits have been repeatedly observed and are determined to be basic characteristics of Yellow Dynamo, which in combination distinguish this Chrysanthemum as a new and distinct cultivar:

1. Nine week response.
2. Strong stems with long peduncles up to 30 cm long.
3. Excellent production per stem; up to 14 good usable fully double flowers per stem.
4. Bright, deep yellow florets, immature florets a light yellow-green; about 300 florets per capitulum.
5. Florets slightly incurved, up to 35 mm long, and are oblong to elliptical with an entire margin and an obtuse tip.
6. Thick capitulum up to 70 mm across.
7. The ability to ship and keep well.

8. Adaptability for cultivation in year around programs.

Of the cultivars known to applicant, the most similar in comparison is the parent cultivar Dynamo from which it is distinguished by its bright, deep yellow flowers. The flowers of Dynamo are white. Yellow Dynamo can also be compared to Yellow Polaris, differing therefrom by its thicker capitulum, larger leaves, and better performance under low light conditions. The flower color and general habit of Yellow Dynamo and Yellow Polaris are similar.

The accompanying photographic drawing shows typical inflorescence and foliage characteristics of Yellow Dynamo, with colors being as nearly true as possible with illustrations of this type. The drawing sheet comprises a black and white photograph of the new cultivar, with one flower being colored to accurately depict flower color.

In the following description, color references are made to The Royal Horticultural Colour Chart. The color values were determined at approximately 9:00 a.m. on July 2, 1986 under 4000 foot candles of light intensity at Parrish, Fla.

Classification:

*Botanical.*—*Chrysanthemum morifolium*, Ramat., cv Yellow Dynamo.

*Commercial.*—Cut cushion spray or cushion pompon.

INFLORESCENCE

A. Capitulum:
- *Form.*—Flat.
- *Type.*—Fully double.
- *Diameter across face.*—70 mm.

B. Corolla of ray florets:
- *Color (general tonality from a distance of three meters).*—Yellow.
- *Color (upper surface).*—12A.
- *Color (under surface).*—12B.

C. Corolla of disc florets: None.

D. Reproductive organs:
- *Androecium.*—None.
- *Gynoecium.*—Present in all florets.

PLANT

A. General appearance:
- *Height.*—1-2 meters at finish.

B. Foliage:

*Color* (*upper surface*).—147A.

*Color* (*under surface*).—147B.

*Shape.*—Deeply lobed and slightly serrated.

I claim:

1. A new and distinct cultivar of Chrysanthemum named Yellow Dynamo, as described and illustrated, and particularly characterized by its strong stems with long peduncles that carry bright, deep yellow flowers; nine week response; excellent production per stem; good shipping and keeping qualities, and its adaptability to year around programs.

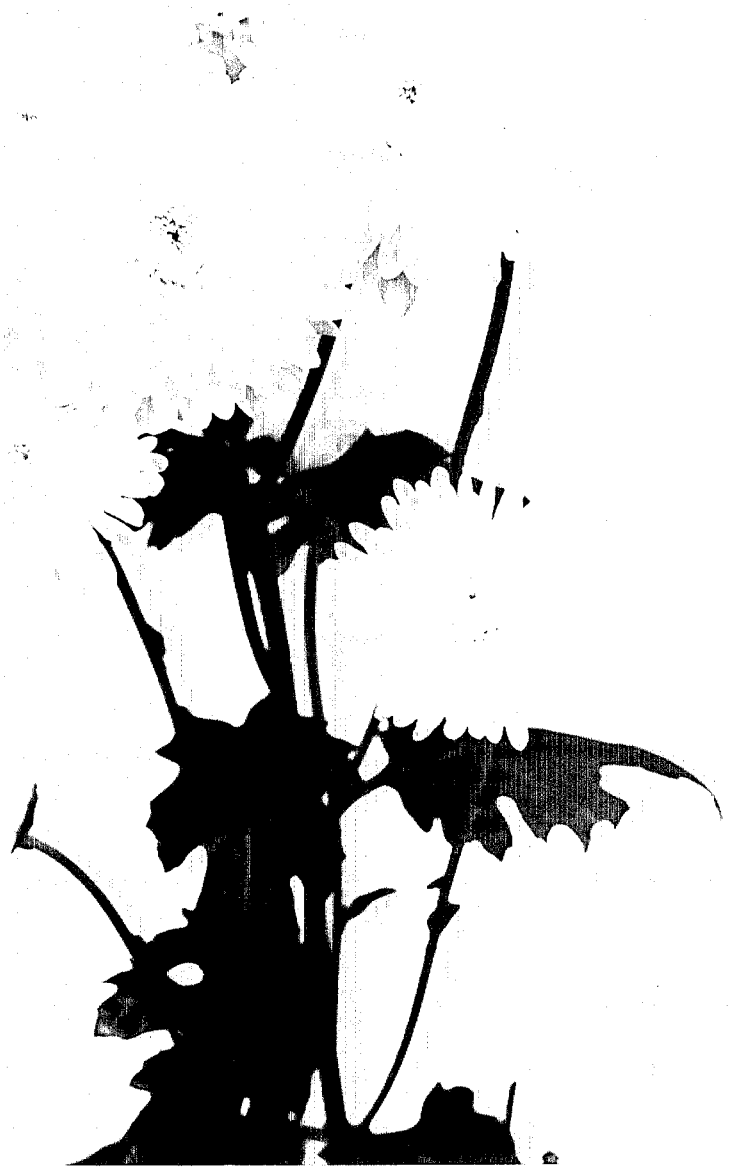

* * * * *